US009237931B2

(12) United States Patent
Gowda et al.

(10) Patent No.: US 9,237,931 B2
(45) Date of Patent: Jan. 19, 2016

(54) STEREOTACTIC ACCESS DEVICES AND METHODS

(75) Inventors: Ashok Gowda, Houston, TX (US);
Roger McNichols, Pearland, TX (US);
Charles Houssiere, Houston, TX (US)

(73) Assignee: Visualase, Inc., Houston, TX (US)

( * ) Notice: Subject to any disclaimer, the term of this patent is extended or adjusted under 35 U.S.C. 154(b) by 108 days.

(21) Appl. No.: 13/592,280

(22) Filed: Aug. 22, 2012

(65) Prior Publication Data
US 2013/0053867 A1  Feb. 28, 2013

Related U.S. Application Data

(60) Provisional application No. 61/525,911, filed on Aug. 22, 2011.

(51) Int. Cl.
*A61B 19/00*  (2006.01)
(52) U.S. Cl.
CPC ............. *A61B 19/201* (2013.01); *A61B 19/203* (2013.01); *A61B 2019/208* (2013.01); *A61B 2019/5483* (2013.01)
(58) Field of Classification Search
CPC .................................................. A61B 2019/208
USPC ........................................ 606/130, 108, 129
See application file for complete search history.

(56) References Cited

U.S. PATENT DOCUMENTS

| 5,752,962 | A * | 5/1998 | D'Urso | 606/130 |
| 5,843,093 | A * | 12/1998 | Howard, III | 606/130 |
| 6,327,491 | B1 * | 12/2001 | Franklin et al. | 600/429 |
| 7,794,469 | B2 * | 9/2010 | Kao et al. | 606/130 |
| 7,824,417 | B2 * | 11/2010 | Magnusson et al. | 606/130 |
| 2002/0038126 | A1 * | 3/2002 | Dominguez. | A61B 17/0642 606/130 |
| 2005/0075649 | A1 | 4/2005 | Bova et al. | |
| 2005/0085719 | A1 * | 4/2005 | Franklin et al. | 600/424 |
| 2011/0190789 | A1 * | 8/2011 | Thiran et al. | 606/130 |

FOREIGN PATENT DOCUMENTS

| EP | 2779924 A1 | 9/2014 |
| WO | WO-01-95822 A2 | 12/2001 |
| WO | WO-2009060394 A1 | 5/2009 |
| WO | WO-2013028811 A1 | 2/2013 |

OTHER PUBLICATIONS

International Preliminary Report on Patentability and Written Opinion mailed on Jan. 21, 2013 for PCT/US2012/051949 claiming benefit of U.S. Appl. No. 61/525,911, filed Aug. 22, 2011 which claims the benefit of U.S. Appl. No. 13/592,280, filed Aug. 22, 2012.
International Search Report and Written Opinion mailed on Jan. 21, 2013 for PCT/US2012/051949 claiming benefit of U.S. Appl. No. 61/525,911, filed Aug. 22, 2011 which claims the benefit of U.S. Appl. No. 13/592,280, filed Aug. 22, 2012.

\* cited by examiner

*Primary Examiner* — Tuan V Nguyen
(74) *Attorney, Agent, or Firm* — Harness, Dickey

(57) ABSTRACT

This invention is directed to devices and methods for stereotactic access, and particularly to a frameless stereotactic access device for accessing a body cavity and methods therefor. In general, a stereotactic device may include portions or features for fixing the device to a portion of a patient's body, such as, for example, a skull, such that the device may be generally spatially fixed in relation to the patient's body or part thereof. The stereotactic device may also generally include portions or features for guiding a medical device or other device at a particular trajectory in relation to the patient's body or part thereof.

15 Claims, 2 Drawing Sheets

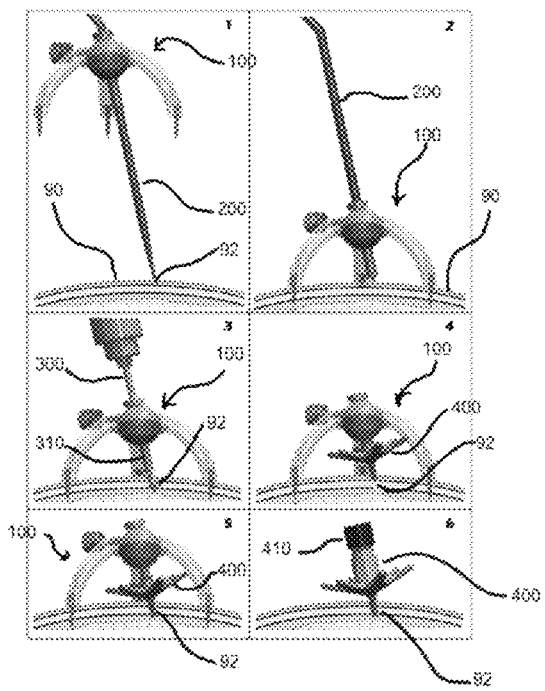
FIG. 2.
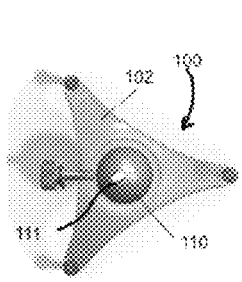
FIG. 3.
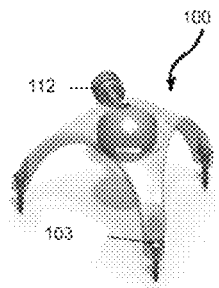
FIG. 3a.
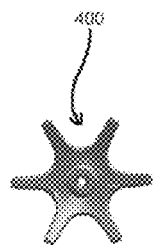
FIG. 3b.
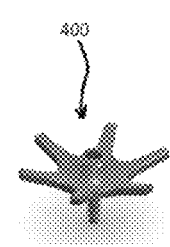
FIG. 3c.
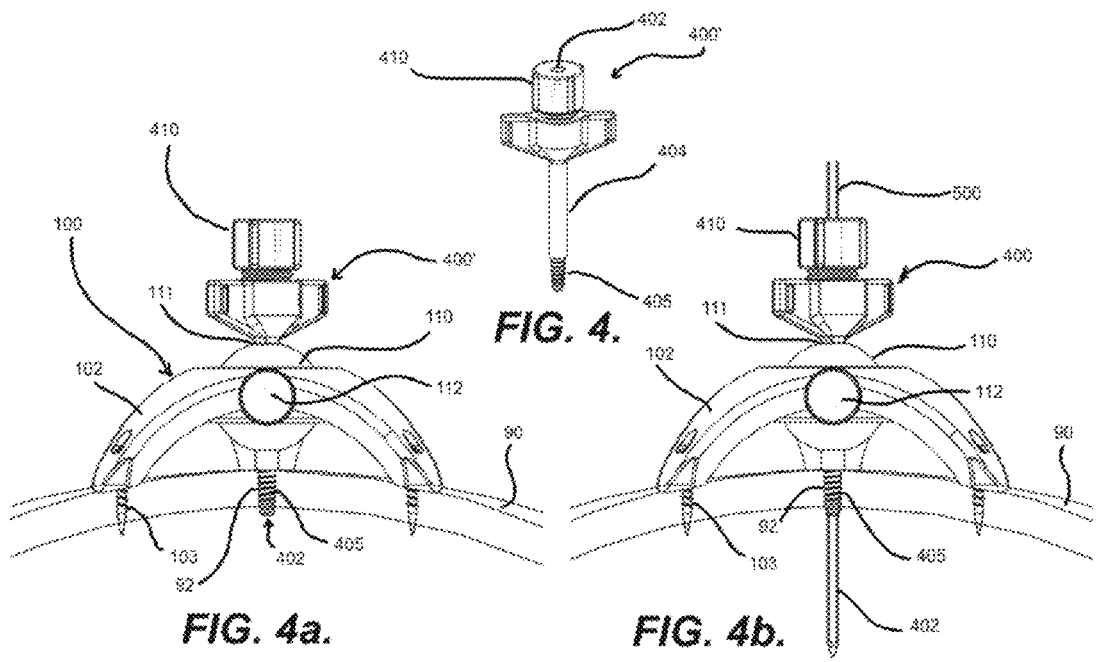
FIG. 4.
FIG. 4a.
FIG. 4b.

STEREOTACTIC ACCESS DEVICES AND METHODS

CROSS-REFERENCE TO RELATED APPLICATIONS

This application claims the priority of U.S. provisional patent application Ser. No. 61/525,911, filed Aug. 22, 2011, and entitled "STEREOTACTIC ACCESS DEVICE", the contents of which are hereby incorporated by reference in its entirety.

FIELD OF THE INVENTION

This invention relates to devices and methods for stereotactic access, and particularly to a frameless stereotactic access device for accessing a body cavity and methods therefor.

BACKGROUND OF THE INVENTION

Stereotactic head frames have a long and proven history in neurosurgery. The two most commonly used are the Leksell (Elekta) and CRW (Integra Neurosciences) frames. In these procedures, a frame is mounted to the head by screwing pins directly against the patient's skull for fixation at four points. The head with attached frame are then imaged by CT or MRI to identify targets, either manually or more frequently with computerized software, in relation to the external frame. Since both the frame and target can be viewed on the images, the distance of the target from given reference points on the frame can be measured in three coordinates. Next in the OR, an arc apparatus is attached to the head frame and adjusted based on the previously measured coordinates and desired trajectory. One in position, a guide is used to drill a hole along a trajectory to the target. These head frames are associated with high accuracy (1-2 mm) for reaching target structures, much of which is achieved by having a permanent fixation between the skull and guide being used for creating the cranial access. Unfortunately, the frame is cumbersome, uncomfortable for patients, and time intensive.

Frameless stereotactic procedures rely on registration of the patient's skull using anatomical landmarks, skin fiducial, or bone fiducials to a pre-acquired MRI or CT scan. In the operating room the orientation of fiducial markers or skin surfaces is registered using stereoscopic cameras on the navigation system to a volume of brain images. Once registration is completed, the navigation system can show the relationship of any registered surgical instruments to patient's brain anatomy. The two major manufacturers of these neuronavigation systems are Medtronic and Brainlabs. Both companies offer accessories which attach to the patients bed to allow twist drill access to a target along a defined trajectory. The drawback to these accessories (Medtronic—Precision Aiming Device and Brainlab Varioguide) are that neither is directly attached to the patient's head, and therefore any movement of the drill is not directly accompanied by a corresponding movement of the head. Both systems require additional time and resource to set up in the operating room. Finally, because skin fiducials are movable in relation to the underlying skull, additional error may be realized from the registration alone.

SUMMARY OF THE INVENTION

This invention is directed to devices and methods for stereotactic access, and particularly to a frameless stereotactic access device for accessing a body cavity and methods therefor. In general, a stereotactic device may include portions or features for fixing the device to a portion of a patient's body, such as, for example, a skull, such that the device may be generally spatially fixed in relation to the patient's body or part thereof. The stereotactic device may also generally include portions or features for guiding a medical device or other device at a particular trajectory in relation to the patient's body or part thereof.

In one aspect, a stereotactic access device includes a plurality of mounting arms which may further include mounting devices or features such that, for example, the stereotactic access device may be mounted securely to a patient's body or part thereof. In some embodiments, the mounting arms may generally be adapted to provide a stable mounting of the stereotactic access device to a patient's body or part thereof. For example, many body parts have curved or irregular surfaces such that stable mounting may be desirable. In an exemplary embodiment, the mounting arms may form at least a stable plane such that when the mounting arms are attached to the patient's body, the stereotactic access device may generally be spatially stable and/or attached securely. In one embodiment, the stereotactic access device may include three mounting arms which may form a stable plane. The mounting arms may also be adapted to conform to the contours of a patient's body or part thereof, such as, for example, a skull. The mounting arms may further be adapted to contour, for example, such that there may be access space between the stereotactic access device and the patient's body and/or portion thereof. This may be desirable, for example, to manipulate a medical device and/or other device between the stereotactic access device and the patient's body and/or portion thereof.

In another aspect, a stereotactic access device includes a mounting and/or guiding feature such that a medical device and/or other device may be mounted to or guided to the stereotactic access device such that, for example, the device may be retained at a particular orientation and/or spatial relationship to the patient's body or part thereof. In some embodiments, the mounting and/or guiding feature may include a rotatable portion, such as an orbitally rotatable and/or swivelable portion, such that the orientation of the portion may be changed with respect to the patient's body, a portion thereof, and/or the rest of the stereotactic access device. In an exemplary embodiment, the mounting and/or guiding feature may include, for example, a rotating sphere which may further include a guide channel to, for example, receive a medical device and/or other device.

In a further aspect, a stereotactic access device includes features for aiding in mounting, positioning and/or registering the position and/or orientation of the stereotactic access device, for example, in relation to the patient's body and/or portion thereof. In some embodiments, the stereotactic access device may include, for example, mounting hardware such as, for example, screws, nails, bolts, pins, and/or any other appropriate mounting hardware or combination thereof. For certain curvatures and/or shapes of a body and/or portion thereof, spacers and/or other adjustment accessories, such as spacers between the end of the mounting arm(s) and the body, may be utilized such that a stable plane may be established with the stereotactic access device. In general, the mounting hardware may provide, for example, stable and/or secure retention and/or fixation of the stereotactic access device to a patient's body and/or portion thereof, such as, for example, to a bone or soft tissue via, for example, mounting arms. In some embodiments, the mounting hardware may also provide and/or act as, for example, fiducial markers for aiding in positioning and/or registering the position and/or orientation of the stereotactic access device, such as, for example, relative to the patient's body and/or portion thereof. For example, the mounting hardware may be registered and/or imaged by a detection modality, such as, for example, magnetic resonance imaging (MRI), X-ray, computerized tomography (CT), ultrasound, and/or any other appropriate detection modality or combination thereof.

In another aspect, a stereotactic access device is utilized in methods for accessing the interior of a patient's body at a particular location and/or along a particular trajectory. In an exemplary embodiment, a method for stereotactic access may include:

Step 1: After registration of the patient and navigation tools, a standard navigation wand may be used to determine and mark a rough entry point, and the patient may then be prepped. The navigation wand may then be inserted into the sphere of the stereotactic access device such that the surgeon may hold both devices, for example, with one hand.

Step 2: Using stereotactic navigation software, the surgeon may find the desired entry point again and may then align the navigation wand with the planned trajectory to a target. The surgeon may then slide the stereotactic access device down onto the patient's body and mounting hardware, such as, for example, three small titanium screws, may then be secured, for example, through the skin and into bone, such as, for example, the skull. The wand may be used again to confirm the trajectory, such as prior to locking the device in place.

Step 3: The surgeon may then remove the navigation wand and replace it with, for example, one of several various sized drill adapters. A stab incision may also be made at the entry site under the stereotactic access device. A surgical drill may then be inserted along the locked trajectory and a twist drill hole may be created through, for example, a bone such as the skull.

Step 4: The drill adapter may then be retracted to optionally allow, for example, a bone screw or anchor to be placed under the stereotactic access device. The drill adapter may be made to fit into the bone screw or anchor's proximal end such that the threads of the screw may fall into the hole created in step 3. A biopsy probe may also be passed directly through an appropriate adapter, for example, such as with its own thumb screw, and may be used to acquire, for example, tissue samples.

Step 5: For placement of probes or electrodes, the surgeon may secure the bone screw by securing it in, for example, the previously drilled hole.

Step 6: The stereotactic access device may be removed, for example, by unscrewing the three screws, and if any stab incisions were created, they may be closed using a single staple or suture. A Touhy-Borst adapter may also be threaded onto the proximal female luer of the bone screw, which may allow applicators to pass through while ensuring a sterile field.

In some embodiments, the stereotactic access device may also be left in place after a hole is drilled. For example, a bone screw may connect to the stereotactic access device such that a continuous sealed channel may be established from the stereotactic access device through the bone screw and into the body. A sealing cap and/or other sealing component may also be included to close off the introducing end of the stereotactic access device.

In other embodiments, the stereotactic access device may be left in place and an introducer may be inserted into the channel of the stereotactic access device and into the drilled hole in the body. The end of the introducer may further include a cap and/or a seal such that the channel may be kept sterile.

In some aspects, the stereotactic access device may be desirable as it may generally be utilized with existing and/or standard practice navigation devices, probes and/or systems, and may thus be adaptable to a diverse number of medical practices with very little additional training and/or the need for specialized equipment. For example, the stereotactic access device may generally be compatible and/or be compatible via adapters to receive a standard navigation probe or wand, treatment devices, drills and/or other equipment used in stereotactic surgery. Further, use of the stereotactic access device may generally be intuitive and aid in surgical usage with a minimal number of moving parts and/or components such that, for example, users may use the stereotactic access device with minimal difficulty, while still being highly versatile in application due to a universal use design.

The present invention together with the above and other advantages may best be understood from the following detailed description of the embodiments of the invention illustrated in the drawings.

BRIEF DESCRIPTION OF THE FIGURES

FIGS. 2-1, 2-2, 2-3, 2-4, 2-5 and 2-6 illustrate the steps of a method of stereotactic access to a patient's body in some embodiments of the present invention;

FIGS. 3 and 3a illustrate an example of a frameless stereotactic access device;

FIGS. 3b and 3c illustrate an example of a bone anchor for use with a frameless stereotactic access device; and FIGS. 4, 4a and 4b illustrate a frameless stereotactic access device with a sealed device introducer.

DETAILED DESCRIPTION OF THE INVENTION

The detailed description set forth below is intended as a description of the presently exemplified devices, methods and materials provided in accordance with aspects of the present invention, and it is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

This invention is directed to devices and methods for stereotactic access, and particularly to a frameless stereotactic access device for accessing a body cavity and methods therefor. In general, a stereotactic device may include portions or features for fixing the device to a portion of a patient's body, such as, for example, a skull, such that the device may be generally spatially fixed in relation to the patient's body or part thereof. The stereotactic device may also generally include portions or features for guiding a medical device or other device at a particular trajectory in relation to the patient's body or part thereof.

In one aspect, a stereotactic access device includes a plurality of mounting arms which may further include mounting devices or features such that, for example, the stereotactic access device may be mounted securely to a patient's body or part thereof. In some embodiments, the mounting arms may generally be adapted to provide a stable mounting of the stereotactic access device to a patient's body or part thereof. For example, many body parts have curved or irregular surfaces such that stable mounting may be desirable. In an exemplary embodiment, the mounting arms may form at least a stable plane such that when the mounting arms are attached to the patient's body, the stereotactic access device may generally be spatially stable and/or attached securely. In one embodiment, the stereotactic access device may include three mounting arms which may form a stable plane. The mounting arms may also be adapted to conform to the contours of a patient's body or part thereof, such as, for example, a skull. The mounting arms may further be adapted to contour, for example, such that there may be access space between the stereotactic access device and the patient's body and/or portion thereof. This may be desirable, for example, to manipulate a medical device and/or other device between the stereotactic access device and the patient's body and/or portion thereof.

Figure 1:
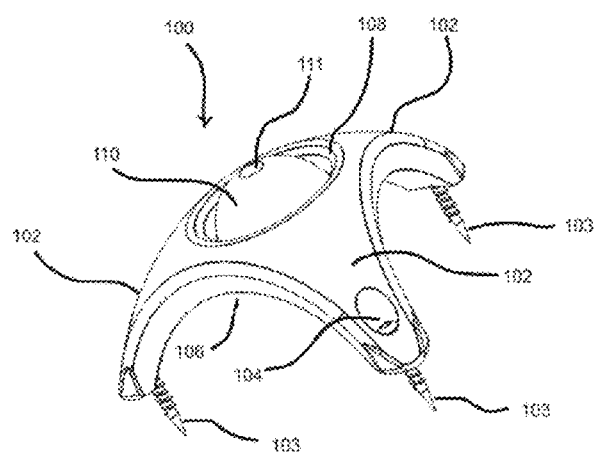
FIGS. 1, 1a, 1b and 1c illustrate a stereotactic access device in some embodiments of the present invention.

FIG. 1 illustrates an example of an embodiment of a stereotactic access device 100. In some embodiments, such as illustrated, the stereotactic access device 100 may generally be a tripod and may include mounting arms 102, such as the three illustrated, which may provide a stable planar platform when mounted to a patient's body. The mounting arms 102 may also generally form a space 106 between the stereotactic access device 100 and a patient's body. This may be desirable such that the area may be freely accessed when the stereotactic access device 100 is in place on the patient's body.

In another aspect, a stereotactic access device includes a mounting and/or guiding feature such that a medical device and/or other device may be mounted to or guided to the stereotactic access device such that, for example, the device may be retained at a particular orientation and/or spatial relationship to the patient's body or part thereof. In some embodiments, the mounting and/or guiding feature may include rotatable portion such that the orientation of the portion may be changed with respect to the patient's body, a portion thereof, and/or the rest of the stereotactic access device. In an exemplary embodiment, the mounting and/or guiding feature may include, for example, a rotating sphere which may further include a guide channel to, for example, receive a medical device and/or other device.

Figure 1A:
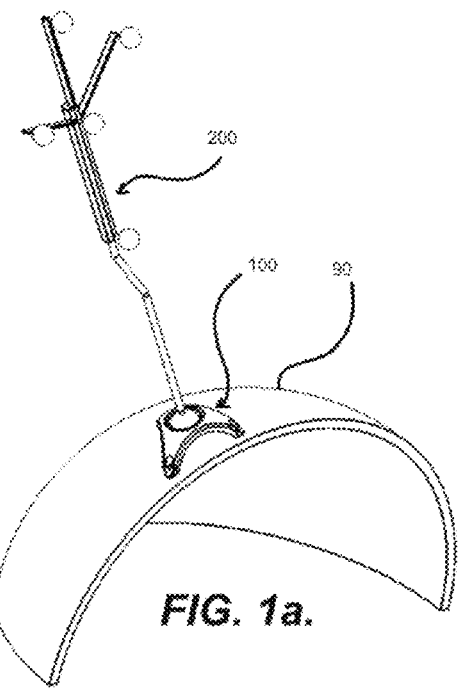
Figure 1B:
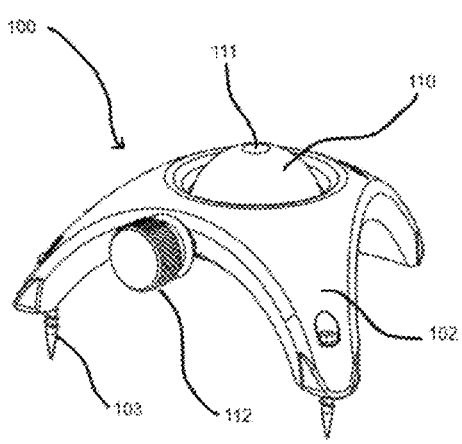
Figure 1C:
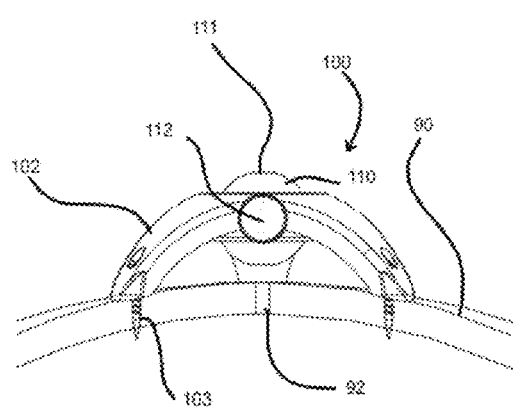

In FIG. 1, the stereotactic access device 100 may include a mounting ball 110, which may be retained in track 108. The mounting ball 110 may generally rotate in the track 108 such that the guide channel 111 may be aligned at the appropriate angle, such as illustrated in FIG. 1a. The mounting ball 100 may thus retain another device, such as, for example, a navigation wand 200, relative to the patient's body 90, such as illustrated in FIG. 1a. The mounting ball 110 may also include a securing part or feature, such as, for example, a securing screw, such that the mounting ball 110 may be locked in a particular orientation, such as with the thumbscrew 112 illustrated in FIGS. 1b and 1c.

In a further aspect, a stereotactic access device includes features for aiding in mounting, positioning and/or registering the position and/or orientation of the stereotactic access device, for example, in relation to the patient's body and/or portion thereof. In some embodiments, the stereotactic access device may include, for example, mounting hardware such as, for example, screws, nails, bolts, pins, and/or any other appropriate mounting hardware or combination thereof. For certain curvatures and/or shapes of a body and/or portion thereof, spacers and/or other adjustment accessories, such as spacers between the end of the mounting arm(s) and the body, may be utilized such that a stable plane may be established with the stereotactic access device. In general, the mounting hardware may provide, for example, stable and/or secure retention and/or fixation of the stereotactic access device to a patient's body and/or portion thereof, such as, for example, to a bone or soft tissue via, for example, mounting arms. In some embodiments, the mounting hardware may also provide and/or act as, for example, fiducial markers for aiding in positioning and/or registering the position and/or orientation of the stereotactic access device, such as, for example, relative to the patient's body and/or portion thereof. For example, the mounting hardware may be registered and/or imaged by a detection modality, such as, for example, magnetic resonance imaging (MRI), X-ray, computerized tomography (CT), ultrasound, and/or any other appropriate detection modality or combination thereof.

As illustrated in FIG. 1, the stereotactic access device 100 may include, for example, screws 103, which may be mounted at the ends of the mounting arms 102. The screws 103 may be, for example, self-tapping such that they may, for example, thread themselves into a surface, such as the patient's body. The screws 103 may also act as fiducials, as discussed above. For certain curvatures of the body and/or other situations requiring adjustment of the apparent dimensions of the mounting arms 102, spacers may be included, such as, for example, about the screws 103 between the end of the mounting arms 102 and the body, such that they may, for further example, effectively lengthen the mounting arms 102.

In another aspect, a stereotactic access device is utilized in methods for accessing the interior of a patient's body at a particular location and/or along a particular trajectory. In an exemplary embodiment, a method for stereotactic access may include:

Step 1: As illustrated in FIG. 2-1, after registration of the patient and navigation tools, a standard navigation wand 200 may be used to determine and mark a rough entry point 92 on the patient's body 90, and the patient may then be prepped. The navigation wand 200 may then be inserted into the sphere of the stereotactic access device 100 such that the surgeon may hold both devices, for example, with one hand.

Step 2: As illustrated in FIG. 2-2, using stereotactic navigation software, the surgeon may find the desired entry point 92 again and may then align the navigation wand 200 with the planned trajectory to a target. The surgeon may then slide the stereotactic access device 100 down onto the patient's body and mounting hardware, such as, for example, three small titanium screws, may then be secured, for example, through the skin and into bone, such as, for example, the skull. The navigation wand 200 may be used again to confirm the trajectory, such as prior to locking the stereotactic access device 100 in place.

Step 3: As illustrated in FIG. 2-3, the surgeon may then remove the navigation wand 200 and replace it with, for example, one of several various sized drill adapters 310. A stab incision may also be made at the entry site 92 under the stereotactic access device 100. A surgical drill 300 may then be inserted along the locked trajectory and a twist drill hole may be created through, for example, a bone such as the skull, at the entry site 92.

Step 4: As illustrated in FIG. 2-4, the drill adapter 310 may then be retracted to optionally allow, for example, a bone screw or anchor 400 to be placed under the stereotactic access device 100. The drill adapter 310 may be made to fit into the bone screw or anchor's 400 proximal end such that the threads of the screw 400 may fall into the hole created in step at the entry site 92. A biopsy probe may also be passed directly through an appropriate adapter, for example, such as with its own thumb screw, and may be used to acquire, for example, tissue samples.

Step 5: As illustrated in FIG. 2-5, for placement of probes or electrodes, the surgeon may secure the bone screw 400 by securing it in, for example, the previously drilled hole at the entry site 92.

Step 6: As illustrated in FIG. 2-6, the stereotactic access device 100 may be removed, for example, by unscrewing the three screws, and if any stab incisions were created, they may be closed using a single staple or suture. A Touhy-Borst adapter 410 may also be threaded onto the proximal female luer of the bone screw 400, which may allow applicators to pass through while ensuring a sterile field.

In some embodiments, the stereotactic access device 100 may also be left in place after a hole at entry site 92 is drilled. For example, a bone screw 400 may connect to the stereotactic access device 100 such that a continuous sealed channel may be established from the stereotactic access device 100 through the bone screw 400 and into the body 90. A sealing cap and/or other sealing component may also be included to close off the introducing end of the stereotactic access device 100.

In other embodiments, such as illustrated in FIGS. 4, 4*a* and 4*b*, the stereotactic access device 100 may be left in place and an introducer 400' may be inserted into the channel 111 of the stereotactic access device 100 and into the drilled hole at the entry site 92 in the body 90. The end of the introducer 400' may further include a cap and/or a seal, such as the sealing cap 410 as illustrated in FIG. 4, such that the channel 402 may be kept sterile. The insertable portion 404 may be retained in the guide channel 111. The insertable end 405 may further be threaded to engage the drilled hole at the entry site 92. A device 500, such as a laser probe and/or other type of medical device, may then be inserted into the channel 402 through the introducer 400' and into the body through the entry site 92, as illustrated in FIG. 4*b*.

Example of Construction of a Frameless Stereotactic Cranial Access Guide

In an example of a stereotactic access device, a frameless stereotactic cranial access guide (FIGS. 3, 3*a*, 3*b* and 3*c*) includes 2 parts—Tripod 100 and a bone screw 400. The tripod 100 (measuring for example 2.5" in diameter and 1.25" in height) may hold several adapters for various navigation wands, drills, and bone screws 400 (measuring for example 1.5" in diameter). Wherever the tripod 100 is located on the cranium, the feet may be seated to allow all three screws to have a solid hold to the skull, due to the planar tripod body design. Space is provided between the patient's skull and the base of the sphere 110 to allow access to the incision/entry point. The sphere 110 press fits into the body of the tripod 100 and swivels in all directions. The through hole 111 in the sphere 110 may fit various adapters for several parts of the procedure. The thumbscrew 112 is used to tighten and secure the sphere 110 in a particular orientation once the desired trajectory is achieved. Three guide screws 103 are located on the tips 102 of the tripod 100 and may secure to the skull and anchor the guide in its position over the skull, such as, for example, over the entry point.

It will be appreciated by those of ordinary skill in the art that the present invention can be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

The invention claimed is:

1. A system comprising:
a stereotactic access device comprising
a tripod having three mounting arms forming a stable planar platform with an access space, wherein each of the mounting arms comprises a respective securing device, and wherein the securing devices are at respective distal ends of the mounting arms and are configured to thread into a bone of a patient, and
a mounting guide having a guide channel,
wherein
the mounting guide is retained in a track in the tripod, wherein distances between the mounting guide and the securing devices are fixed,
the mounting arms are arched to provide the access space, which is present between a distal side of the mounting guide and the bone of the patient while the securing devices are secured to the bone of the patient, and
each of the securing devices comprises a respective registerable fiducial in a fixed positional relationship relative to the tripod; and
a bone screw configured to extend through the mounting guide and screw into the bone of the patient, and wherein the bone screw comprises a channel through which a second device may extend to enter the bone of the patient.

2. The system of claim 1, wherein each of the securing devices comprises a respective self-tapping screw.

3. The system of claim 1, wherein the registerable fiducials are detectable by a magnetic resonance imaging (MRI) system, an X-ray system, a computerized tomography (CT) system, or an ultrasound system.

4. The system of claim 1, wherein the guide channel is adapted to receive a navigation wand.

5. The system of claim 1, wherein the mounting guide is a mounting ball.

6. The system of claim 5, further comprising a locking screw adapted to lock the mounting guide in an orientation relative to the tripod.

7. The system of claim 1, further comprising spacers at the ends of the mounting arms.

8. The system of claim 1, wherein:
the mounting guide is spherical shaped and swivels;
the track is cup-shaped and receives the mounting guide; and
the mounting guide is press-fit into the track.

9. A system comprising:
a stereotactic access device comprising
a tripod having three mounting arms forming a stable planar platform with an access space, wherein each of the mounting arms comprises a respective securing device, and wherein the securing devices are at respective distal ends of the mounting arms and are configured to thread into a bone of a patient, and
a mounting guide having a guide channel,
wherein
the mounting guide is retained in a track in the tripod, wherein distances between the mounting guide and the securing devices are fixed,
the mounting arms are arched to provide the access space, which is present between a distal side of the mounting guide and the bone of the patient while the securing devices are secured to the bone of the patient, and each of the securing devices comprises a respective registerable fiducial in a fixed positional relationship relative to the tripod; and a bone screw configured to (i) contact the distal side of the mounting guide, or (ii) partially fit into a proximal side of the mounting guide, wherein the bone screw comprises a first portion, an insertable portion, and a threaded portion, the first portion remains on the proximal side of the mounting guide, the insertable portion extends through the mounting guide, the threaded portion screws into the bone of the patient, and the first portion, the insertable portion, and the threaded portion provide a channel through which a device may extend to enter the bone of the patient.

10. The system of claim 9, further comprising a Toughy-Borst adapter configured to (i) attach to a proximal side of the bone screw, and (ii) receive the device prior to the being received by the bone screw.

11. A system comprising:

a stereotactic access device comprising a tripod having three mounting arms forming a stable planar platform with an access space, wherein each of the mounting arms comprises a respective securing device, and wherein the securing devices are at respective distal ends of the mounting arms, and a mounting guide having a guide channel, wherein the mounting guide is retained in a track in the tripod, wherein each of the securing devices comprises a respective registerable fiducial in a fixed positional relationship relative to the tripod; and a bone screw connected to and disposed on a distal side of the mounting guide, wherein the bone screw has a threaded portion, which is configured to be screwed into a bone of a patient, and a channel through which a second device may extend to enter the bone of the patient.

12. The stereotactic access device of claim 11, wherein:
the mounting guide is spherical shaped and swivels;
the track is cup-shaped and receives the mounting guide; and
the mounting guide is press-fit into the track.

13. The system of claim 11, wherein:
the bone screw comprises a first portion, an insertable portion, and a threaded portion;
the first portion remains on a proximal side of the mounting guide;
the insertable portion extends through the mounting guide;
the threaded portion screws into the bone of the patient; and
the first portion, the insertable portion, and the threaded portion provide a channel through which a second device may extend to enter the bone of the patient.

14. The system of claim 13, further comprising a Toughy-Borst adapter configured to (i) attach to a proximal side of the bone screw, and (ii) receive the second device prior to the second device being received by the bone screw.

15. A system comprising:

a stereotactic access device comprising a tripod having three mounting arms forming a stable planar platform with an access space, wherein each of the mounting arms comprises a respective securing device, and wherein the securing devices are at respective distal ends of the mounting arms and are configured to thread into a bone of a patient, and a mounting guide having a guide channel, wherein the mounting guide is retained in a track in the tripod, wherein distances between the mounting guide and the securing devices are fixed, the mounting arms are arched to provide the access space, which is present between a distal side of the mounting guide and the bone of the patient while the securing devices are secured to the bone of the patient, and each of the securing devices comprises a respective registerable fiducial in a fixed positional relationship relative to the tripod; and a bone screw comprising a threaded portion and an insertable portion, wherein the threaded portion is configured to be screwed into the bone of the patient, wherein the insertable portion is configured to be retained in the guide channel, and wherein the bone screw further comprising a channel through which a second device may extend to enter the bone of the patient.

* * * * *